(12) United States Patent
Ma et al.

(10) Patent No.: US 8,923,768 B2
(45) Date of Patent: *Dec. 30, 2014

(54) RELIABLE COMMUNICATIONS FOR WIRELESS DEVICES

(71) Applicant: Abbott Medical Optics Inc., Santa Ana, CA (US)

(72) Inventors: Dung Ma, Garden Grove, CA (US); Fred Lee, Irvine, CA (US)

(73) Assignee: Abbott Medical Optics Inc., Santa Ana, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/765,537

(22) Filed: Feb. 12, 2013

(65) Prior Publication Data

US 2013/0149967 A1 Jun. 13, 2013

Related U.S. Application Data

(63) Continuation of application No. 11/250,982, filed on Oct. 13, 2005, now Pat. No. 8,380,126.

(51) Int. Cl.

| | |
|---|---|
| *H04B 7/00* | (2006.01) |
| *H04B 17/00* | (2006.01) |
| *H04L 1/22* | (2006.01) |
| *H04B 1/74* | (2006.01) |
| *A61B 5/00* | (2006.01) |
| *A61B 17/00* | (2006.01) |

(52) U.S. Cl.
CPC .............. *H04B 17/00* (2013.01); *A61B 5/0002* (2013.01); *H04L 1/22* (2013.01); *A61B 5/7475* (2013.01); *H04B 1/74* (2013.01); *A61B 2017/00973* (2013.01)
USPC ......................................... 455/41.2; 455/509

(58) Field of Classification Search
USPC ................ 455/41.1, 41.2, 41.3, 404.1, 404.2, 455/66.1, 450, 452.2; 433/77, 98
See application file for complete search history.

(56) References Cited

U.S. PATENT DOCUMENTS

| | | |
|---|---|---|
| 1,848,024 A | 3/1932 | Owen |
| 3,076,904 A | 2/1963 | Claus et al. |

(Continued)

FOREIGN PATENT DOCUMENTS

| | | |
|---|---|---|
| EP | 56019 A1 | 7/1982 |
| EP | 619993 A1 | 10/1994 |

(Continued)

OTHER PUBLICATIONS

European Search Report for Application No. EP10164058, mailed on Jun. 25, 2010, 2 pages.

(Continued)

*Primary Examiner* — Ping Hsieh
(74) *Attorney, Agent, or Firm* — Abbott Medical Optics Inc.

(57) ABSTRACT

A method and apparatus for connectivity management of a wireless device is provided, such as a wireless medical device. The method comprises providing a wireless connection between at least two medical devices, the at least two medical devices comprising a primary medical device and a secondary medical device, causing the primary medical device to transmit and the secondary medical device to receive state signals wirelessly across a plurality of communication data channels, and reporting a non-active state for one of the plurality of data channels from the primary medical device to the secondary medical device using the plurality of communication data channels.

14 Claims, 5 Drawing Sheets

(56) References Cited

U.S. PATENT DOCUMENTS

| | | |
|---|---|---|
| 3,116,697 A | 1/1964 | Theodore |
| 3,439,680 A | 4/1969 | Thomas, Jr. |
| 3,526,219 A | 9/1970 | Lewis |
| 3,781,142 A | 12/1973 | Zweig |
| 3,857,387 A | 12/1974 | Shock |
| 4,017,828 A | 4/1977 | Watanabe et al. |
| 4,037,491 A | 7/1977 | Newbold |
| 4,189,286 A | 2/1980 | Murry et al. |
| 4,193,004 A | 3/1980 | Lobdell et al. |
| 4,564,342 A | 1/1986 | Weber et al. |
| 4,590,934 A | 5/1986 | Malis et al. |
| 4,665,621 A | 5/1987 | Ackerman et al. |
| 4,706,687 A | 11/1987 | Rogers et al. |
| 4,757,814 A | 7/1988 | Wang et al. |
| 4,773,897 A | 9/1988 | Scheller et al. |
| 4,837,857 A | 6/1989 | Scheller et al. |
| 4,920,336 A | 4/1990 | Meijer |
| 4,933,843 A | 6/1990 | Scheller et al. |
| 4,954,960 A | 9/1990 | Lo et al. |
| 4,965,417 A | 10/1990 | Massie |
| 4,983,901 A | 1/1991 | Lehmer |
| 4,998,972 A | 3/1991 | Chin et al. |
| 5,006,110 A | 4/1991 | Garrison et al. |
| 5,026,387 A | 6/1991 | Thomas |
| 5,039,973 A | 8/1991 | Carballo |
| 5,091,656 A | 2/1992 | Gahn |
| 5,125,891 A | 6/1992 | Hossain et al. |
| 5,160,317 A | 11/1992 | Costin |
| 5,195,960 A | 3/1993 | Hossain et al. |
| 5,195,961 A | 3/1993 | Takahashi et al. |
| 5,195,971 A | 3/1993 | Sirhan |
| 5,230,614 A | 7/1993 | Zanger et al. |
| 5,249,121 A | 9/1993 | Baum et al. |
| 5,268,624 A | 12/1993 | Zanger |
| 5,271,379 A | 12/1993 | Phan et al. |
| 5,282,787 A | 2/1994 | Wortrich |
| 5,323,543 A | 6/1994 | Steen et al. |
| 5,342,293 A | 8/1994 | Zanger |
| 5,351,676 A | 10/1994 | Putman |
| 5,388,569 A | 2/1995 | Kepley |
| 5,454,783 A | 10/1995 | Grieshaber et al. |
| 5,470,211 A | 11/1995 | Knott et al. |
| 5,520,652 A | 5/1996 | Peterson |
| 5,549,461 A | 8/1996 | Newland |
| 5,554,894 A | 9/1996 | Sepielli |
| 5,561,575 A | 10/1996 | Eways |
| 5,580,347 A | 12/1996 | Reimels |
| 5,591,127 A | 1/1997 | Barwick et al. |
| 5,657,000 A | 8/1997 | Ellingboe |
| 5,676,530 A | 10/1997 | Nazarifar |
| 5,676,650 A | 10/1997 | Grieshaber et al. |
| 5,693,020 A | 12/1997 | Rauh |
| 5,697,898 A | 12/1997 | Devine |
| 5,700,240 A | 12/1997 | Barwick et al. |
| 5,733,256 A | 3/1998 | Costin |
| 5,745,647 A | 4/1998 | Krause |
| 5,747,824 A | 5/1998 | Jung et al. |
| 5,777,602 A | 7/1998 | Schaller et al. |
| 5,805,998 A | 9/1998 | Kodama |
| 5,830,176 A | 11/1998 | Mackool |
| 5,843,109 A | 12/1998 | Mehta et al. |
| 5,879,298 A | 3/1999 | Drobnitzky et al. |
| 5,883,615 A | 3/1999 | Fago et al. |
| 5,899,674 A | 5/1999 | Jung et al. |
| 5,928,257 A | 7/1999 | Kablik et al. |
| 5,983,749 A | 11/1999 | Holtorf |
| 6,002,484 A | 12/1999 | Rozema et al. |
| 6,024,428 A | 2/2000 | Uchikata |
| 6,062,829 A | 5/2000 | Ognier |
| 6,077,285 A | 6/2000 | Boukhny |
| 6,086,598 A | 7/2000 | Appelbaum et al. |
| 6,117,126 A | 9/2000 | Appelbaum et al. |
| 6,150,623 A | 11/2000 | Chen |
| 6,179,829 B1 | 1/2001 | Bisch et al. |
| 6,219,032 B1 | 4/2001 | Rosenberg et al. |
| 6,251,113 B1 | 6/2001 | Appelbaum et al. |
| 6,260,434 B1 | 7/2001 | Holtorf |
| 6,360,630 B2 | 3/2002 | Holtorf |
| 6,368,269 B1 | 4/2002 | Lane |
| 6,411,062 B1 | 6/2002 | Baranowski et al. |
| 6,424,124 B2 | 7/2002 | Ichihara et al. |
| 6,436,072 B1 | 8/2002 | Kullas et al. |
| 6,452,120 B1 | 9/2002 | Chen |
| 6,452,123 B1 | 9/2002 | Chen |
| 6,491,661 B1 | 12/2002 | Boukhny et al. |
| 6,511,454 B1 | 1/2003 | Nakao et al. |
| 6,632,214 B2 | 10/2003 | Morgan et al. |
| 6,674,030 B2 | 1/2004 | Chen et al. |
| 6,830,555 B2 | 12/2004 | Rockley et al. |
| 6,852,092 B2 | 2/2005 | Kadziauskas et al. |
| 6,862,951 B2 | 3/2005 | Peterson et al. |
| 6,962,488 B2 | 11/2005 | Davis et al. |
| 6,962,581 B2 | 11/2005 | Thoe |
| 7,012,203 B2 | 3/2006 | Hanson et al. |
| 7,070,578 B2 | 7/2006 | Leukanech et al. |
| 7,073,083 B2 * | 7/2006 | Litwin et al. .................. 713/324 |
| 7,103,344 B2 | 9/2006 | Menard |
| 7,167,723 B2 | 1/2007 | Zhang |
| 7,169,123 B2 | 1/2007 | Kadziauskas et al. |
| 7,236,766 B2 | 6/2007 | Freeburg |
| 7,236,809 B2 | 6/2007 | Fischedick et al. |
| 7,242,765 B2 | 7/2007 | Hairston |
| 7,244,240 B2 | 7/2007 | Nazarifar et al. |
| 7,289,825 B2 | 10/2007 | Fors et al. |
| 7,300,264 B2 | 11/2007 | Souza |
| 7,316,664 B2 | 1/2008 | Kadziauskas et al. |
| 7,336,976 B2 | 2/2008 | Ito |
| 7,381,917 B2 | 6/2008 | Dacquay et al. |
| 7,439,463 B2 | 10/2008 | Brenner et al. |
| 7,470,277 B2 | 12/2008 | Finlay et al. |
| 7,526,038 B2 | 4/2009 | McNamara |
| 7,883,521 B2 | 2/2011 | Rockley et al. |
| 7,921,017 B2 | 4/2011 | Claus et al. |
| 2001/0023331 A1 | 9/2001 | Kanda et al. |
| 2001/0047166 A1 | 11/2001 | Wuchinich |
| 2001/0051788 A1 | 12/2001 | Paukovits et al. |
| 2002/0019215 A1 | 2/2002 | Romans |
| 2002/0019607 A1 | 2/2002 | Bui |
| 2002/0045887 A1 | 4/2002 | DeHoogh et al. |
| 2002/0070840 A1 | 6/2002 | Fischer et al. |
| 2002/0098859 A1 | 7/2002 | Murata |
| 2002/0137007 A1 | 9/2002 | Beerstecher |
| 2002/0179462 A1 | 12/2002 | Silvers |
| 2003/0047434 A1 | 3/2003 | Hanson et al. |
| 2003/0083016 A1 | 5/2003 | Evans et al. |
| 2003/0108429 A1 | 6/2003 | Angelini et al. |
| 2003/0125717 A1 | 7/2003 | Whitman |
| 2003/0224729 A1 | 12/2003 | Arnold |
| 2003/0226091 A1 | 12/2003 | Platenberg et al. |
| 2004/0037724 A1 | 2/2004 | Haser et al. |
| 2004/0193182 A1 | 9/2004 | Yaguchi et al. |
| 2004/0212344 A1 | 10/2004 | Tamura et al. |
| 2004/0224641 A1 | 11/2004 | Sinn |
| 2005/0054971 A1 | 3/2005 | Steen et al. |
| 2005/0069419 A1 | 3/2005 | Cull et al. |
| 2005/0070859 A1 | 3/2005 | Cull et al. |
| 2005/0109595 A1 | 5/2005 | Mezhinsky et al. |
| 2005/0118048 A1 | 6/2005 | Traxinger |
| 2005/0130098 A1 | 6/2005 | Warner |
| 2005/0197131 A1 | 9/2005 | Ikegami |
| 2005/0209560 A1 | 9/2005 | Boukhny et al. |
| 2005/0245888 A1 | 11/2005 | Cull |
| 2005/0261628 A1 | 11/2005 | Boukhny et al. |
| 2006/0035585 A1 | 2/2006 | Washiro |
| 2006/0036180 A1 | 2/2006 | Boukhny et al. |
| 2006/0046659 A1 * | 3/2006 | Haartsen et al. ........... 455/67.11 |
| 2006/0078448 A1 | 4/2006 | Holden |
| 2006/0145540 A1 | 7/2006 | Mezhinsky |
| 2006/0219049 A1 | 10/2006 | Horvath et al. |
| 2006/0236242 A1 | 10/2006 | Boukhny et al. |
| 2007/0016174 A1 | 1/2007 | Millman et al. |
| 2007/0049898 A1 | 3/2007 | Hopkins et al. |
| 2007/0060926 A1 | 3/2007 | Escaf |
| 2007/0073214 A1 | 3/2007 | Dacquay et al. |

(56) References Cited

U.S. PATENT DOCUMENTS

| | | |
|---|---|---|
| 2007/0073309 A1 | 3/2007 | Kadziauskas et al. |
| 2007/0078379 A1 | 4/2007 | Boukhny et al. |
| 2007/0249942 A1 | 10/2007 | Salehi et al. |
| 2008/0033342 A1 | 2/2008 | Staggs |
| 2008/0066542 A1 | 3/2008 | Gao |
| 2008/0112828 A1 | 5/2008 | Muri et al. |
| 2008/0114289 A1 | 5/2008 | Muri et al. |
| 2008/0114290 A1 | 5/2008 | King et al. |
| 2008/0114291 A1 | 5/2008 | Muri et al. |
| 2008/0114300 A1 | 5/2008 | Muri et al. |
| 2008/0114311 A1 | 5/2008 | Muri et al. |
| 2008/0114312 A1 | 5/2008 | Muri et al. |
| 2008/0114372 A1 | 5/2008 | Edwards et al. |
| 2008/0114387 A1 | 5/2008 | Hertweck et al. |
| 2008/0125697 A1 | 5/2008 | Gao |
| 2008/0125698 A1 | 5/2008 | Gerg et al. |
| 2008/0146989 A1 | 6/2008 | Zacharias |
| 2008/0243105 A1 | 10/2008 | Horvath |
| 2008/0262476 A1 | 10/2008 | Krause et al. |
| 2008/0281253 A1 | 11/2008 | Injev et al. |
| 2008/0294087 A1 | 11/2008 | Steen et al. |
| 2009/0005712 A1 | 1/2009 | Raney |
| 2009/0005789 A1 | 1/2009 | Charles |
| 2010/0280435 A1 | 11/2010 | Raney et al. |
| 2011/0092887 A1 | 4/2011 | Wong et al. |
| 2011/0092924 A1 | 4/2011 | Wong et al. |
| 2011/0092962 A1 | 4/2011 | Ma et al. |
| 2011/0098721 A1 | 4/2011 | Tran et al. |
| 2011/0160646 A1 | 6/2011 | Kadziauskas et al. |

FOREIGN PATENT DOCUMENTS

| | | | |
|---|---|---|---|
| EP | 1010437 | A1 | 6/2000 |
| EP | 1072285 | A1 | 1/2001 |
| EP | 1113562 | A1 | 7/2001 |
| EP | 1310267 | A2 | 5/2003 |
| EP | 1469440 | A2 | 10/2004 |
| EP | 1550406 | A2 | 7/2005 |
| EP | 1704839 | A1 | 9/2006 |
| EP | 1787606 | A1 | 5/2007 |
| EP | 1849443 | A1 | 10/2007 |
| EP | 1849444 | A1 | 10/2007 |
| EP | 1867349 | A1 | 12/2007 |
| EP | 1873501 | A1 | 1/2008 |
| EP | 1900347 | A1 | 3/2008 |
| EP | 1925274 | A2 | 5/2008 |
| ES | 2264369 | A1 | 12/2006 |
| GB | 2230301 | A | 10/1990 |
| GB | 2352887 | A | 2/2001 |
| JP | 2008188110 | A | 8/2008 |
| WO | WO-9220310 | A1 | 11/1992 |
| WO | WO-9317729 | A1 | 9/1993 |
| WO | WO-9324082 | A1 | 12/1993 |
| WO | WO-9632144 | A1 | 10/1996 |
| WO | WO-9818507 | A1 | 5/1998 |
| WO | WO-9917818 | A1 | 4/1999 |
| WO | WO-0000096 | A1 | 1/2000 |
| WO | WO-0070225 | A1 | 11/2000 |
| WO | WO-0122696 | A1 | 3/2001 |
| WO | WO-0234314 | A1 | 5/2002 |
| WO | 03102878 | A1 | 12/2003 |
| WO | WO-2004096360 | A1 | 11/2004 |
| WO | WO-2004114180 | A1 | 12/2004 |
| WO | WO-2005084728 | A2 | 9/2005 |
| WO | WO-2005092023 | A2 | 10/2005 |
| WO | WO-2005092047 | A2 | 10/2005 |
| WO | WO-2006101908 | A2 | 9/2006 |
| WO | WO-2006125280 | A1 | 11/2006 |
| WO | WO-2007121144 | A1 | 10/2007 |
| WO | WO-2007143677 | A2 | 12/2007 |
| WO | WO-2007143797 | A1 | 12/2007 |
| WO | WO-2008030872 | A1 | 3/2008 |
| WO | WO-2008060859 | A1 | 5/2008 |
| WO | WO-2008060902 | A1 | 5/2008 |
| WO | WO-2008060995 | A1 | 5/2008 |
| WO | WO-2010054146 | A1 | 5/2010 |
| WO | WO-2010054225 | A2 | 5/2010 |

OTHER PUBLICATIONS

International Preliminary Report on Patentability and Written Opinion for Application No. PCT/US2006/38978, mailed on Apr. 16, 2008, 8 pages.

International Search Report for Application No. PCT/US2006/38978, mailed on Feb. 27, 2007, 3 pages.

Merritt R., et al., Wireless nets starting to link medical gear [online] 2004 [retrieved on Feb. 12, 2007]. Retrieved from the Internet: < http://www.eetimes.com/showArticle.jht ml">.

Boyd, "Preparing for the Transition" in: The Art and the Science of Cataract Surgery, Chapter 7, 2001, pp. 93-133.

International Preliminary Report on Patentability and Written Opinion for Application No. PCT/US2006/39868, mailed on Apr. 16, 2008, 6 pages.

International Search Report for Application No. PCT/US2006/39868, mailed on Nov. 12, 2007, 3 pages.

Phacoemulsification, [online] [retrieved on Jul. 1, 2009]. Retrieved from the Internet: <http://en.wikipedia.org/wiki/Phacoemulsification>, 2 pages.

\* cited by examiner

RELIABLE COMMUNICATIONS FOR WIRELESS DEVICES

This application is a continuation application and claims priority to U.S. application Ser. No. 11/250,982, entitled "Reliable Communications For Wireless Devices", filed on Oct. 13, 2005, the entire contents of which are hereby incorporated by reference in their entirety for all purposes as if fully set forth herein.

BACKGROUND OF THE INVENTION

1. Field of the Invention

The present invention relates generally to the field of medical systems, and more specifically to managing reliable, high availability communications for wireless medical devices.

2. Description of the Related Art

Traditionally, medical system products transmit control signals over a fixed wire or cable. Current advancements in wireless communications techniques, including short-range radio and light wave technology, enable designers to employ wireless connections to transmit control signals and other data, thus removing the need for a traditional fixed wire or cable. Examples of removable or non-fixed devices include monitors or monitoring equipment, test equipment, remote control devices, and so forth.

The rapid advancement and proliferation of short-range radio technology affords medical system product designers and manufacturers the ability to create and deploy non-fixed subsystems and devices without need for a conventional fixed physical communication cable. For example, non-fixed devices meeting or complying with the Institute of Electrical and Electronics Engineers (IEEE) 802.11g and Ericsson Bluetooth™ specifications provide short-range radio technology to enable for wireless communications. These technologies allow for wireless transmission of signals over short distances between computers and other electronic devices. Bluetooth™ enabled devices are capable of an approximate 10-meter transmission range at data rates up to 720 kilobits/sec, and can provide better security features than devices implementing IEEE 802.11g communications.

Although typically not well suited for medical applications, line-of-sight wireless light wave technology, including Infrared Data Association (IrDA) techniques, may also be employed by product designers to realize wireless connections.

Implementing either the Bluetooth™ or IEEE 802.11g specifications will yield a communications path between wireless non-fixed devices and subsystems. Each specification also addresses providing an interference resistant communications path with automatic error detection and correction capabilities for transmitting and receiving of control signals, data, and information.

However, the Bluetooth™ and IEEE 802.11g specifications only address the wireless transmission and reception of data, control signals and information across a single communications path. Non-fixed wireless medical subsystems and devices require a continuous, reliable, and high availability communications network to ensure uninterrupted operation of an instrument host system. The above-cited specifications do not provide for a continuous, reliable, and highly available communication experience under all operating theater conditions. Due to the critical health support requirements for medical equipment and the potential catastrophic consequences of a communications connection failure in such equipment, effective deployment of medical systems incorporating wireless devices require a highly reliable communications management scheme to ensure a reliable connection from the instrument host system is constantly available to fielded non-fixed wireless subsystems and devices. Neither of the foregoing specifications guarantees this high a level of reliable communications management.

Active wireless medical devices, when used under normal operation, are exposed to numerous sources of electrical and magnetic interference, environmental conditions, and reliability issues. Electrical and magnetic interference may cause a loss of signal strength or degrade the signal quality sufficient to cause a wireless communications path to disconnect. For example, a single wireless Bluetooth™ connection requires a few seconds to re-establish a failed connection. During this reconnect time period, the surgeon can lose remote control of the surgical system and be unable to control the medical equipment. This reconnection time delay is not desirable or suitable for safety critical devices or equipment. footpedal. In addition, a "zero position switch" footpedal incorporates the ability to detect the footpedal returning to a non-active state independent of the linear position detection, thus serving as a fail-safe trigger. If this independent fail-safe trigger is directed through a single wireless channel, communication of this trigger is subject to a single-point-of-failure arrangement that loses any redundancy benefit.

Reliable wireless device communication management schemes in this environment must therefore not only provide a reliable continuous communications path but also a mechanism for monitoring and reporting the signal strength and signal quality condition for wireless subsystems and devices when subjected to external interference and environmental conditions found in the operating theater.

Thus it would be advantageous to offer an architecture and design that provide wireless operated subsystems and devices a reliable and highly available communications management scheme to ensure safe and continuous peripheral product operation in an environment where the wireless device and controlled instrument host are subjected to conditions that may interfere with the communication path.

SUMMARY OF THE INVENTION

According to one aspect of the present design, there is provided a method for managing communications between a plurality of medical devices. The method comprises providing a wireless connection between at least two medical devices, the at least two medical devices comprising a primary medical device and a secondary medical device, causing the primary medical device to transmit and the secondary medical device to receive state signals wirelessly across a plurality of communication data channels, and reporting a non-active state for one of the plurality of data channels from the primary medical device to the secondary medical device using the plurality of communication data channels.

According to another aspect of the present design, there is provided a connectivity management system. The connectivity management system comprises a wireless controller configured to communicate over a plurality of communications data channels. The connectivity management system further comprises a wireless medical device configured to communicate over the plurality of communications data channels, wherein the wireless controller and wireless medical device are connected and exchange state information across the plurality of communications data channels and alternate communication between at least two of the communications data channels based on observed channel quality.

These and other advantages of the present invention will become apparent to those skilled in the art from the following detailed description of the invention and the accompanying drawings.

DESCRIPTION OF THE DRAWINGS

The present invention is illustrated by way of example, and not by way of limitation, in the figures of the accompanying drawings in which.

DETAILED DESCRIPTION OF THE INVENTION

The present design provides a method and apparatus for managing reliable, high availability communications for wireless devices. A communications management arrangement or subsystem may provide a mechanism for monitoring and reporting the health and status of a plurality of data channels used to connect wireless devices, particularly in instances where the wireless device or devices operate in a medical theater, including but not limited to an operating room. The communications management subsystem may include a novel redundant wireless data channel arrangement to eliminate any potential single-points-of-failure within the communications network. The present design method is directed to managing a reliable redundant wireless communications network to support a wireless device, typically employed in a medical scenario but applicable in other scenarios, where communications management includes the monitoring health and status of one or more data channels, reporting health and status of the data channels, indicating current communications path connection quality condition to a user, and automatically switching to a backup communication path when necessary to ensure continuous reliable high availability communications.

While the present design may be used in various environments and applications, it will be discussed herein with a particular emphasis on a medical or hospital environment, where a surgeon or health care practitioner performs. For example, one embodiment of the present design is a phacoemulsification system or method using a surgical system that incorporates a wireless medical device, such as a wireless footswitch, to control the surgical system.

The term "wireless device" or "wireless medical device" or "non-fixed wireless device" or the like as used herein means a device capable of receiving and/or transmitting information wirelessly, i.e. over the air, using either a radio, light wave (e.g. infrared) or other communication technique that does not require a physical connection, such as a wire. Wireless devices that may realize the reception and transmission of data include, but are not limited to, those devices meeting or complying with the Institute of Electrical and Electronics Engineers (IEEE) 802.11 and Ericson Bluetooth™ specifications for short range radio technology, or an Infrared Data Association (IrDA) light wave technique.

The present design provides an arrangement that enables users of wireless medical devices to continue uninterrupted work independent of individual wireless data channel health. This arrangement provides monitoring and reporting information services in regard to the wireless medical device communications network condition, including providing automatic switching to a backup communications channel when necessary to continue transmitting and receiving data to ensure continuous, reliable, and safe use.

Figure 1:
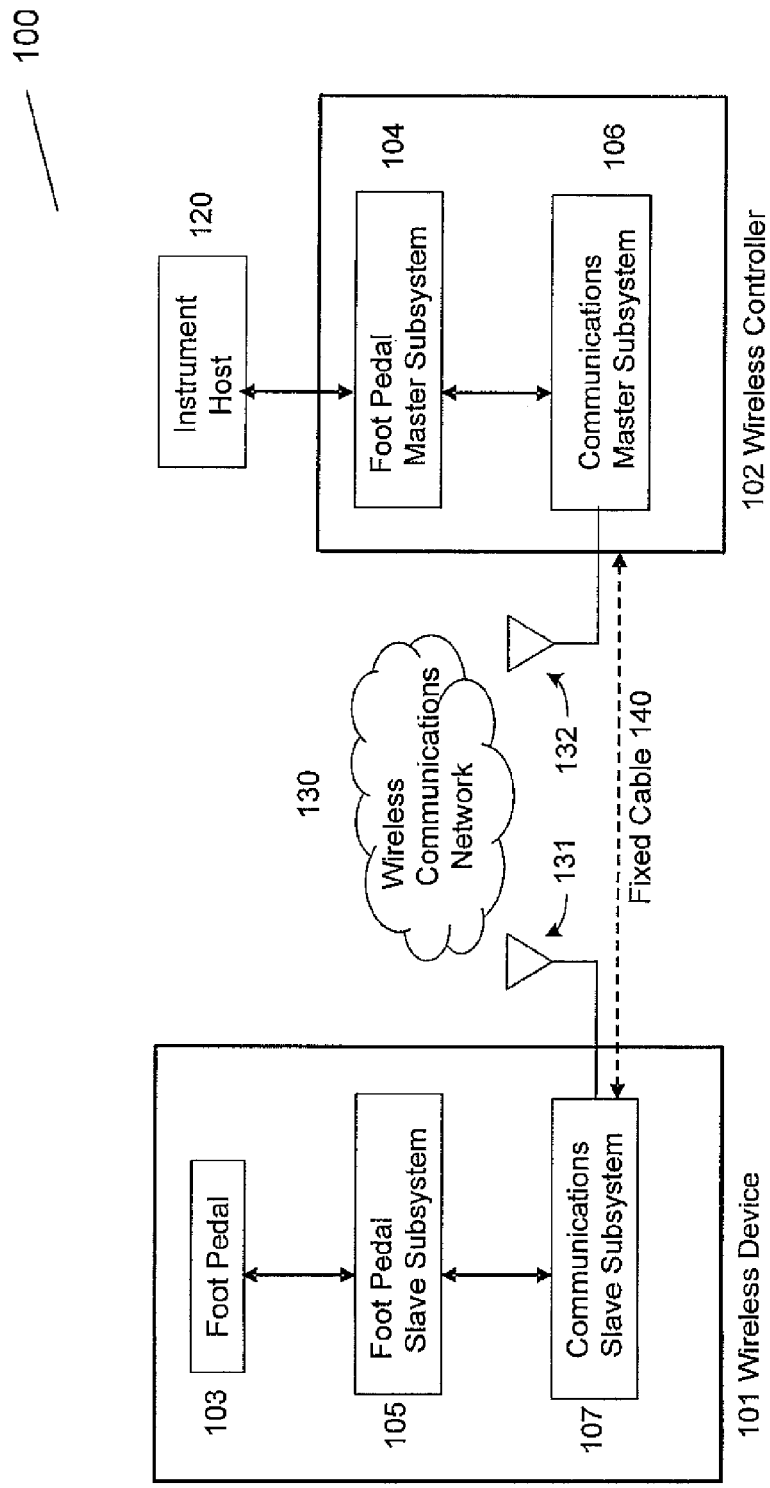
FIG. 1 is a block diagram illustrating the present design components and interfaces of a wireless medical system with a communications management subsystem.

FIG. 1 illustrates the present design components and interfaces of a wireless medical system 100, where the particular embodiment illustrated in FIG. 1 contemplates that the wireless or remote device is a footpedal. The medical system 100 in this embodiment includes a wireless device 101, a wireless controller 102, an instrument host system 120, and a wireless communications network 130. A footpedal 103 may transmit control signals relating internal physical switch position information (not shown in this view; see FIG. 4) as input to a footpedal slave subsystem 105. The footpedal slave subsystem 105 may provide data indicating physical and virtual switch position information to a communications slave subsystem 107. The communication slave subsystem 107, typically comprising a transmitter and receiver operating, for example, using the wireless 802.11g or Bluetooth™ protocols, may transmit this data using a wireless communication network 130 via antenna 131, or alternatively a fixed cable 140 wired mode.

One approach to digital electronic footpedal control system, especially for a medical device, is described in U.S. Pat. No. 4,983,901, entitled "Digital Electronic Foot Control for Medical Apparatus and the Like", issued Jan. 8, 1991, the entirety of which is incorporated herein by reference. A typical footpedal design is further provided in U.S. Pat. No. 5,268,624, entitled "Footpedal Control with User-selectable Operational Ranges" issued Dec. 7, 1993, the entirety of which is incorporated herein by reference.

The wireless communications network 130 may employ any network communications protocol sufficient for serving the purposes of communications network 130. Additionally, the term "communications network" or "communications system" as used herein is used in its most expansive sense and applies to any communications system through which any information may be transferred to and from a wireless device, and includes, without limitation, transmission by static, active, dynamic communications protocols or otherwise. While the present design may use various communication protocols, it will be discussed herein implementing and complying with Ericsson's Bluetooth™ protocol specification. Slight changes may be made to the enclosed to enable operation using other or complementary communications protocols, and the use and implementation of the present design using these other protocols is intended to be within the scope of the current design.

Note that while discussed with regard to dual Bluetooth™ channels herein, more than two channels may be employed for additional redundancy, and different protocols may be used on different channels. As an example, a first channel may run according to a Bluetooth™ protocol while a second channel may run according to an 802.11g protocol. Different parameters, such as different transmission frequencies or data rates may also be employed over the plurality of channels offered in the current design. Other protocols may be employed, including but not limited to IrDA (infrared data).

As a further option, the system may provide at least one active channel together with cross checking capability provided by another channel, typically utilizing a cross checking mechanism such as checksums to evaluate signal quality and/or correctness. In such an implementation, the active channel constantly transmits data while the secondary channel transmits cross checking information, and upon failure of the cross check, transmission switches to the secondary channel.

From wireless communication network 130 via antenna 132, the wireless controller 102 receives wireless device 101 transmissions via a communication master subsystem 106, typically comprising a transmitter and receiver. The communications master subsystem 106 receives and forwards data, including but not limited to information such as footpedal position and state parameters, to the footpedal master subsystem 104. Position and state information, may include but is not limited to representing relative pitch and yaw travel of the footpedal 103, as well as buttons, switches, or other input devices on footpedal 103. Moreover, the communication slave subsystem 107 may provide redundant wireless connections supporting a primary communication path, and one or more backup communication paths to ensure reliable exchange of data.

The footpedal master subsystem may transfer this data to an instrument host 120. The instrument host 120 may use the received data to control and operate the behavior of various embedded features and functions including irrigation, aspiration, electrical cauterization, and various cutting actions, such as phacoemulsification and vitrectomy procedures, and providing pressure for posterior ocular segment surgery, such as viscous fluid injection. The instrument host 120 may use the data to effectuate a switch between handpieces, modes, or modules, such as switching between a phacoemulsification procedure and a vitreous cutting procedure. Such a switch may be effectuated by the operator providing an indication on a switch or button on footpedal 103 that indicates a desired switch between procedures or modules.

In a similar manner, the instrument host 120 may provide information to the footpedal master subsystem 104, including but not limited to information such as control signals indicating the amplitude and duration to command the footpedal 103 vibration device, such as a vibration motor or solenoid actuator (not shown), sufficient to provide tactile feedback to the surgeon. In addition, the instrument host 120 may provide information to the footpedal master subsystem 104 for the purposes of providing cues, such as activating status lights and emitting sounds, on the footpedal to alert the operator. The footpedal master subsystem 104 may forward information received from the instrumentation host 120 to the communications master subsystem 106. The communication master subsystem 106 may transmit this information across the wireless communications network 130 to the wireless device 101 communication slave subsystem 107. The communications slave subsystem 107 may deliver the control signal information to the footpedal slave subsystem 105, which in turn may deliver these signals to the footpedal 103; thus resulting in the operation of the vibration motor or other feedback mechanisms within the footpedal 103 in accordance with the supplied control signal amplitude and duration.

Furthermore, the communications master subsystem 106 and the communications slave subsystem 107 may monitor the health and status of the primary and backup Bluetooth data channels, including but not limited to data channel signal quality and strength. Details describing this aspect of the communications master subsystem 106 and the communications slave subsystem 107 are provided below.

While depicted as multiple elements, footpedal master subsystem 104 and communications master subsystem 106 may alternatively be comprised of a single firmware device or a set of distributed firmware devices that fulfill the functionality of pedal master subsystem 104 and communications master subsystem 106. Additionally, while depicted as multiple elements, footpedal slave subsystem 105 and communications slave subsystem 107 may also be comprised of a single firmware device or a set of distributed firmware devices that fulfill the functionality of pedal master subsystem 104 and communications master subsystem 106.

Figure 2:
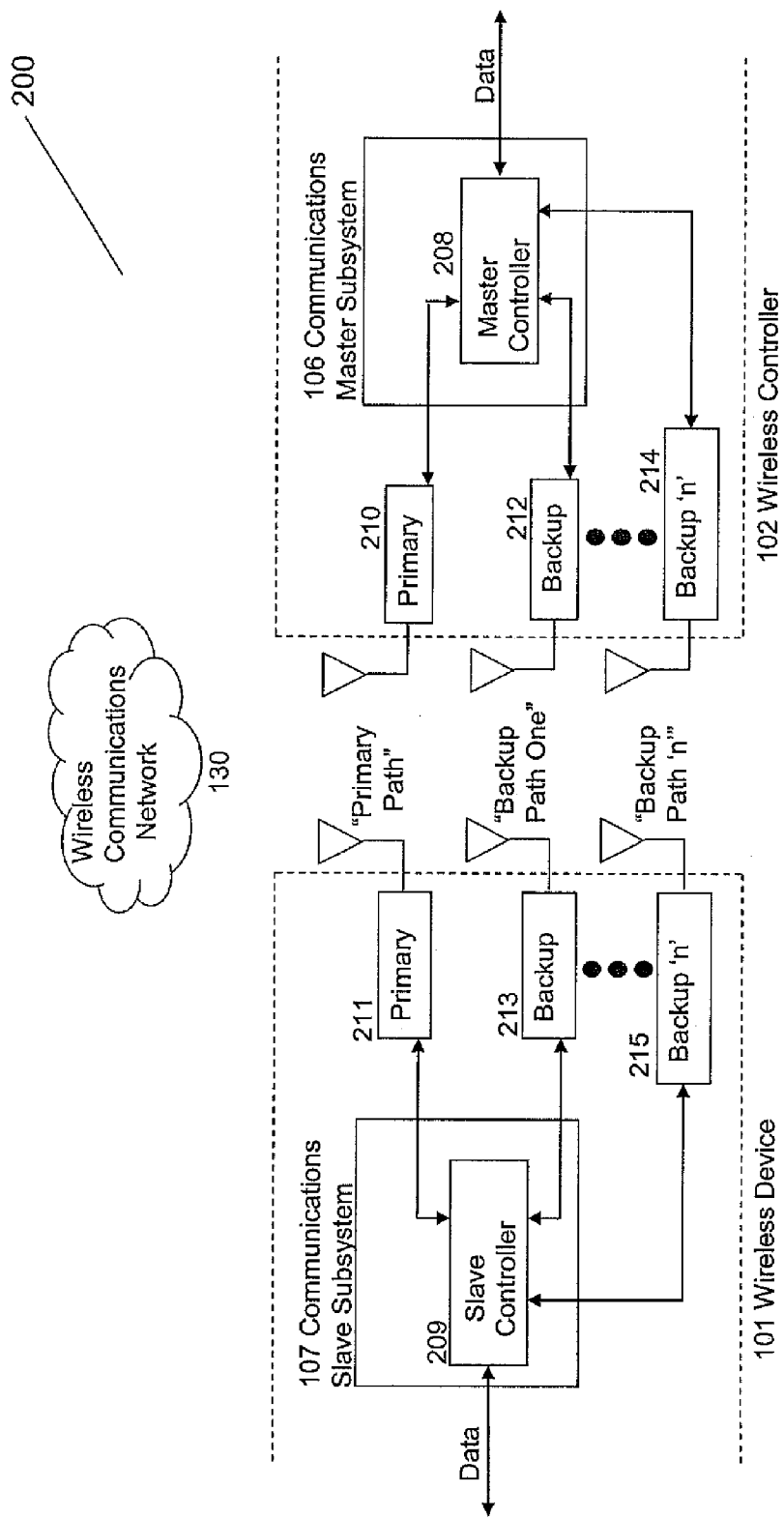
FIG. 2 illustrates components of the present design and interfaces of a primary and backup wireless communications network.

FIG. 2 illustrates components of the present design and interfaces of the wireless communications network 130 to the wireless device 101 and wireless controller 102, where the embodiment illustrated in FIG. 2 contemplates that the wireless transmission and reception of data and information is realized using a primary communication path and one or more secondary backup communication paths.

Data is typically transferred in many protocols in the form of packets of data, but other data transfer formats may be employed. Packets typically contain fields such as headers and lower level protocol information embedded in the packet. Data is transferred via packets using certain common protocols. In an alternate embodiment of the present design, communications and packets could be divided between channels, such as pitch packets for a footpedal movement on one channel and yaw packets for footpedal movement on the other. Such a design would enable faster data transfer, may save power, and may enable cross checking as discussed below, but failure of one channel would require relatively immediate transfer to the other channel and carrying both pitch and yaw packets in this example over the remaining channel.

At the beginning of the surgical day, the user powers on the instrument host 120. During the instrument start-up sequence, the communications master subsystem 106 within the wireless controller 102 determines if a physical connection supporting a fixed cable 140 wired mode is available (not shown in this view; see FIG. 1). If a physical cable is present, the communications master subsystem 106 may activate and establish communications with the wireless device 101 communications slave subsystem 107 across this fixed cable 140 as in typical conventional systems.

In the situation or mode where a physical cable or wire is not present, or where the user chooses to operate in the wireless mode, the wireless controller 102 may invoke a wireless mode by activating and establishing communications with the wireless device 101 communications slave subsystem 107. In the wireless mode, a wireless communications network 130 replaces the fixed cable 140 found in the wired mode to enable exchange of control signals, data, and information between the wireless controller 102 and the wireless device 101.

In this mode, the wireless controller 102 communications master subsystem 106 initiates a wireless device-searching mode to locate and pair with an available wireless device 101 communications slave subsystem 107 to establish a primary wireless communications path across the wireless communications network 130. The wireless controller 102 searches for a unique wireless device 101 using, for example, Bluetooth™ short-range radio techniques. Searching is complete when the correct wireless device 101 is located. At this point, the wireless controller 102 'pairs-up' or 'matches' with the unique wireless device 101 to enable communication of control signal and other device information, such as battery condition. The specific techniques and details associated with Bluetooth™ searching and "pairing" mechanism are generally known to those skilled in the art. Alternate searching and locating techniques may be employed depending on the transmission protocol employed. For example, 802.11g may employ link control procedures known to those skilled in the art and specified by the standard, while a protocol such as IrDa may employ optical locating and searching techniques again known to those skilled in the art.

Subsequently, the communications master subsystem 106 establishes one or more backup wireless communication paths in a similar manner over the wireless communications network 130. In this example, the master controller 208 imbedded within the communications master subsystem 106 establishes a primary connection through Bluetooth primary 210 transceiver subsystem and establishes a backup connection through Bluetooth backup 212 transceiver subsystem. If more than one backup communication path is present and available, the master controller also establishes these communication paths as additional backup connections between 214 and 215 and so forth.

The footpedal master and footpedal slave subsystems, 104 and 105 respectively (refer to FIG. 1), may operate in this embodiment using one or more Bluetooth™ data channels. A successful start-up sequence provides a reliable and high availability redundant communications network between the instrument host 120 and footpedal 103.

During the surgical day, when the instrument host is powered on and operational, the instrument host 120 generates information for conveyance to the footpedal 103. For example, the instrument host 120 may request the footpedal subsystem 105 to "set" or program a specific inactive range for both left and right yaw, provide a programmable threshold to the footpedal subsystem 105 for both left and right virtual switches and buttons (not shown in this view), or request the footpedal subsystem to report an installed firmware version number, serial number, or other identifying information. The master controller 208 provides the same information, in the form of a data stream, for transmission to both the primary communications path at 210 and the backup communications path at 212. In one embodiment, the master controller 208 manages the transmission of the same data stream across both the primary and backup communications paths by first transmitting the data stream across the primary communications path, and then switching to the backup communications path and transmitting the same data stream as originally provided to the primary communication path, or vice versa. This method provides redundant communications between the wireless controller 102 and the wireless device 101. The master controller 208 manages the alternating or 'flip-flopping' between the primary and backup communications path in a manner wherein both paths are never transmitting at the same time.

Alternating between channels ensures that two copies of the same data stream are transmitted to the communications slave subsystem 107 within the wireless device 101. Moreover, the master controller 208 may continuously monitor the health and status of all active paths. Monitoring the health and status may include measuring signal strength, signal quality, or checking data integrity and observing other relevant parameters to determine current path connection condition and reporting the measured result to the communications master subsystem 106. The wireless device 101 may report additional observed non-fixed device management information, including but not limited to current battery charge condition, not pertaining to communications path integrity through the communications network 130 to the wireless controller 102. In addition, the communications path health and status observed by the communications slave subsystem 107 may be delivered to the footpedal slave subsystem 105 for presentation to the user. If either the primary or backup data communications path becomes disconnected during use, the footpedal slave subsystem 105 may provide a visual alert, an audible alert, and any combination thereof to the user. For example, the visual alert may be realized by blinking an LED when either path becomes disconnected, wherein a constantly lit LED may indicate both communications paths are connected and available for use. Similarly, a periodic audible alert may be sounded when either communications path becomes disconnected.

Certain additional safety or beneficial mechanisms may be provided, typically all incurring a cost or performance issue. One alternate embodiment of the present design may include a transmission arrangement wherein data is transmitted on one channel until a failure is sensed and then switching to the second channel upon sensing the failure. The advantage to such a design is the ability to save power, but the down side can be encountered when channel failure is not sensed quickly enough or channels cannot be switched quickly enough to preserve data. However, if power savings is a consideration and constant uninterrupted performance is less critical, such a design may be employed.

Also, a shutoff safety mechanism or a notification may be employed when signal strength or quality on both channels drops below a certain threshold. Such a "fail safe" mode or state may be employed when both channels encounter transmission problems, and the system may in one embodiment switch from wireless transmission of signals to transmission across fixed cable 140. When both channels are not performing adequately, as judged by the specifics of the environment, the system may shut down or notify operators, such as by audio and/or visual cue. The audio and/or visual cue indicates that a dual channel or multiple channel signal transmission problem exists. Such an implementation can be useful in crowded, tight, or noisy environments where required placement of the devices may inhibit signal transmission, and the presentation of audio or visual cues may facilitate a successful reorienting of devices when initial orienting causes poor signalling conditions.

FIG. 3, with reference to FIGS. 1 and 2, illustrates components of the present design and interfaces of the communications management subsystem master controller 208 switching from a primary data channel to a backup data channel when subjected to interference that cause the primary data channel to disconnect. The embodiment illustrated in FIG. 3 contemplates that the wireless transmission and reception of data and information across the primary and backup data channels are realized using a communication protocol such as Bluetooth™ short-range radio technology.

Figure 3A:
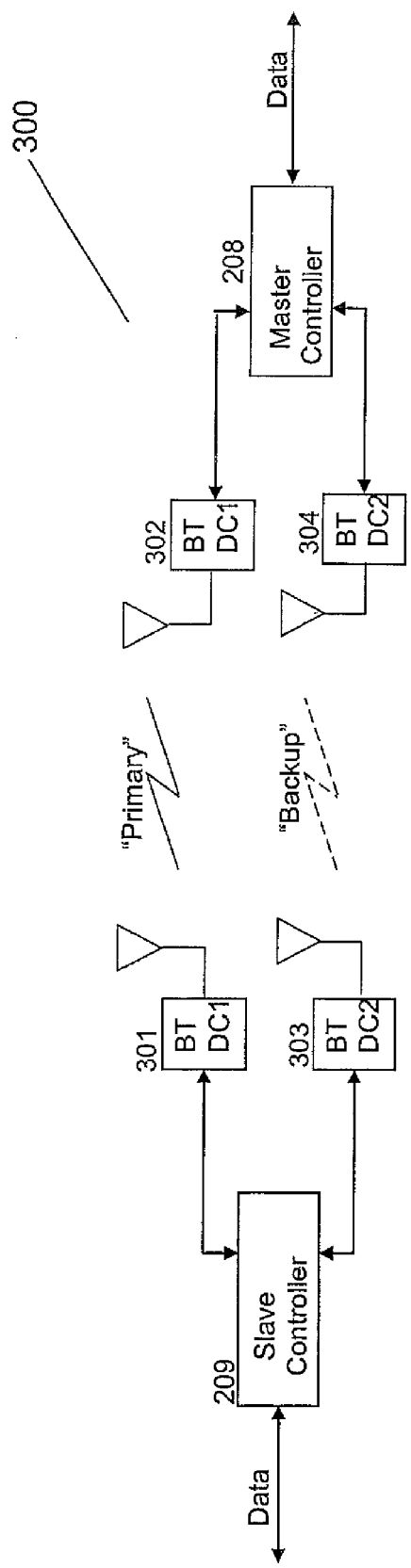
FIG. 3A shows components of the present design and interfaces of a communications management subsystem establishing a primary and a backup communication path.

Initially, the communications master subsystem 106 initiates a wireless device-searching mode utilizing Bluetooth™ data channel one at 302 to locate and pair with an available Bluetooth™ data channel one (BT DC1) at 301 to establish a primary wireless communications data channel over the wireless communications network 130. Subsequently, the communications master subsystem 106 initiates a wireless device-searching mode utilizing Bluetooth™ data channel two (BT DC2) at 304 to locate and pair with an available Bluetooth™ data channel two (BT DC2) at 303 to establish a backup wireless communications data channel over the wireless communications network 130. The primary and backup data channels, as shown in FIG. 3A, can provide a bi-directional redundant connection between the instrument host 120 and the footpedal 103. Data may now be communicated across these channels using the alternating communication technique described previously. Note that if non-bidirectional protocols are employed, an alternate embodiment may be that one data channel engages in one way communication when not in active use, i.e. when the channel has failed or been turned off.

Figure 3B:
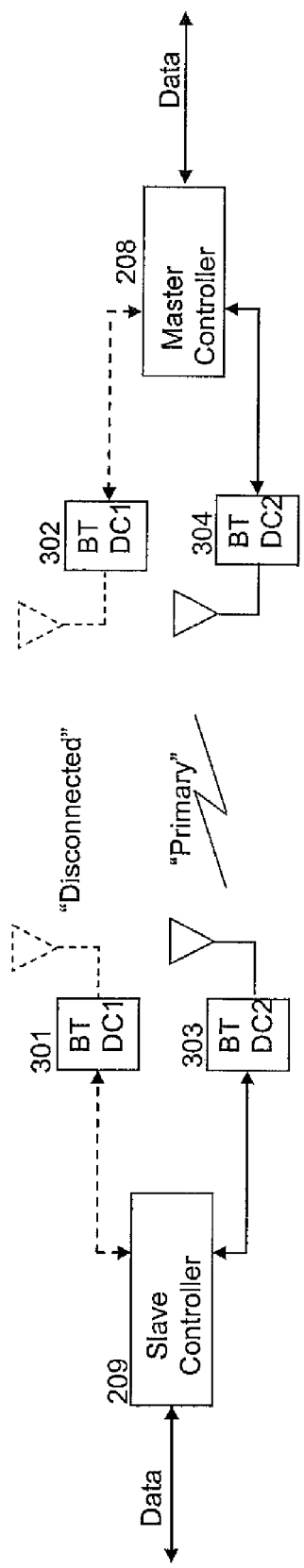
FIG. 3B illustrates components and interfaces of a communications management subsystem switching from a failed primary data channel to a backup data channel.

The master controller 208 and slave controller 209 may provide, including but not limited to, Cyclic Redundancy Codes (CRC) checksum validation, path control, and data validation to manage the communication of data across each data channel (i.e. primary and backup). If the master controller 208 detects that the primary data channel between points 302 and 301 is lost, corrupted, or unstable due to interference or other causes, the master controller 208 promotes the backup data channel between points 304 and 303 to become the primary data channel as shown in FIG. 3B. The newly promoted data channel two (BT DC2) between points 304 and 303 continues to operate as the primary data channel until or even when the failed data channel one is restored. During this operational aspect, the slave controller 209 may observe that receiving Bluetooth™ data channel one (BT DC1) at 301 is no longer able to receive data transmitted by Bluetooth™ data channel one (BT DC1) at 302. In this situation, the slave controller 209 automatically switches to receiving Bluetooth™ data channel two (BT DC2) at 303 as the primary channel and continues to receive data uninterrupted as transmitted by Bluetooth™ data channel two (BT DC2) at 304. As a result, no data interruption occurs during the surgery or procedure being performed.

In a similar manner, the master controller 208 may promote the backup data channel two as primary whenever a signal quality, or any combination thereof is observed. This method of promotion continues during the surgical day to ensure reliable and high availability of the communicated data stream between the instrument host 120 and the footpedal 103. Moreover, if additional backup data channels are available, the present design may promote one of these additional backup data channels to replace the failed data channel, and may return the failed data channel to the backup channel pool when restored.

As an alternative power management scheme, one embodiment of the current design may include the ability to transmit more power on a primary data channel and less power on a secondary cross checking or complimentary channel, thereby decreasing overall power requirements or increasing power transmission on the primary channel.

During the surgical day, when the instrument host is powered on and operational, the footpedal 103 generates information, including but not limited to pedal position and state information, for conveyance to the instrument host 120. The slave controller 209 within the wireless device 101 manages the transmission of information generated by the footpedal 103 to the master controller 208. The slave controller 209 provides the same footpedal information to transmitting Bluetooth™ data channel one at 301 and transmitting Bluetooth™ data channel two at 302. Alternate protocols or different protocols may be employed, such as one channel of IrDA or Bluetooth™ and one channel of 802.11g. Furthermore, the slave controller 209 manages the transmission of the same data stream across both the primary and backup Bluetooth™ data channels by first transmitting the data stream across the primary channel, and then switching to the backup data channel and transmitting the same data stream as provided to the primary data channel, thus providing redundant communications between the wireless device 101 and the wireless controller 102. The slave controller 209 manages the alternating or "flip-flopping" between the primary and backup data channel such that both channels are typically never transmitting at the same time, but are alternately transmitting data separated by small time amounts, such as in the millisecond, microsecond or sub-microsecond range. Data transmission on different channels may transition as desired or required, such as data being first transmitted over the backup channel and second over the primary channel. Alternately, certain blocks of data may be transferred over the primary channel, then those blocks and new blocks over the secondary channel, and then the new blocks and further blocks over the primary channel, or an interleaved data transfer pattern. The method of alternating between channels ensures that two copies of the same data stream are transmitted as rapidly as possible to the communications master subsystem 106 within the wireless controller 102.

Moreover, the slave controller 209 may continuously monitor the health and status of all active data channels. Monitoring the health and status may include measuring signal strength, signal quality, checking data integrity and observing other relevant parameters to determine current data channel connection condition and reporting the measured result to the communications slave subsystem 107.

Note that while certain operations of dual channel transmission are explained within this description in a specific manner, such as operation over a primary channel and subsequent operation on a secondary channel, either channel can operate as primary and another as secondary at any time during operation. It is to be understood that these designations and explanations are offered as examples, and are not intended to be limiting in any way.

If the slave controller 209 detects that the primary data channel is lost, corrupted, or unstable due to interference or other causes, the slave controller 209 promotes the backup channel to become the primary data channel. The newly promoted backup channel continues to operate as the primary data channel, and continues after the originally failed data channel is restored (no need to revert or switch back). During this operational aspect, the master controller 208 may observe that receiving Bluetooth™ data channel one at 302 is no longer able to receive data transmitted by transmitting Bluetooth™ data channel one at 301. In this situation, the slave controller 209 automatically switches to receiving Bluetooth™ data channel two at 304 and continues to receive data without interruption.

In a similar manner, the slave controller 209 may promote the backup data channel to primary whenever a predefined threshold representing signal strength, signal quality, or any combination thereof is observed. This method of promotion continues during the surgical day to ensure reliable and high availability of the communicated data stream between the footpedal 103 and the instrument host 120.

While in use, the wireless communication connection may be subjected to interference or other failure modes and may fall below an operational threshold. The foregoing design enables the wireless device 101 and the wireless controller 102 to reliably communicate information during the day and used in normal operation. In the embodiment illustrated, the wireless device 101 may be a footpedal, but another remote control device may be employed using this communications management arrangement or subsystem, including devices not in communication with the instrument host 120.

Figure 4:
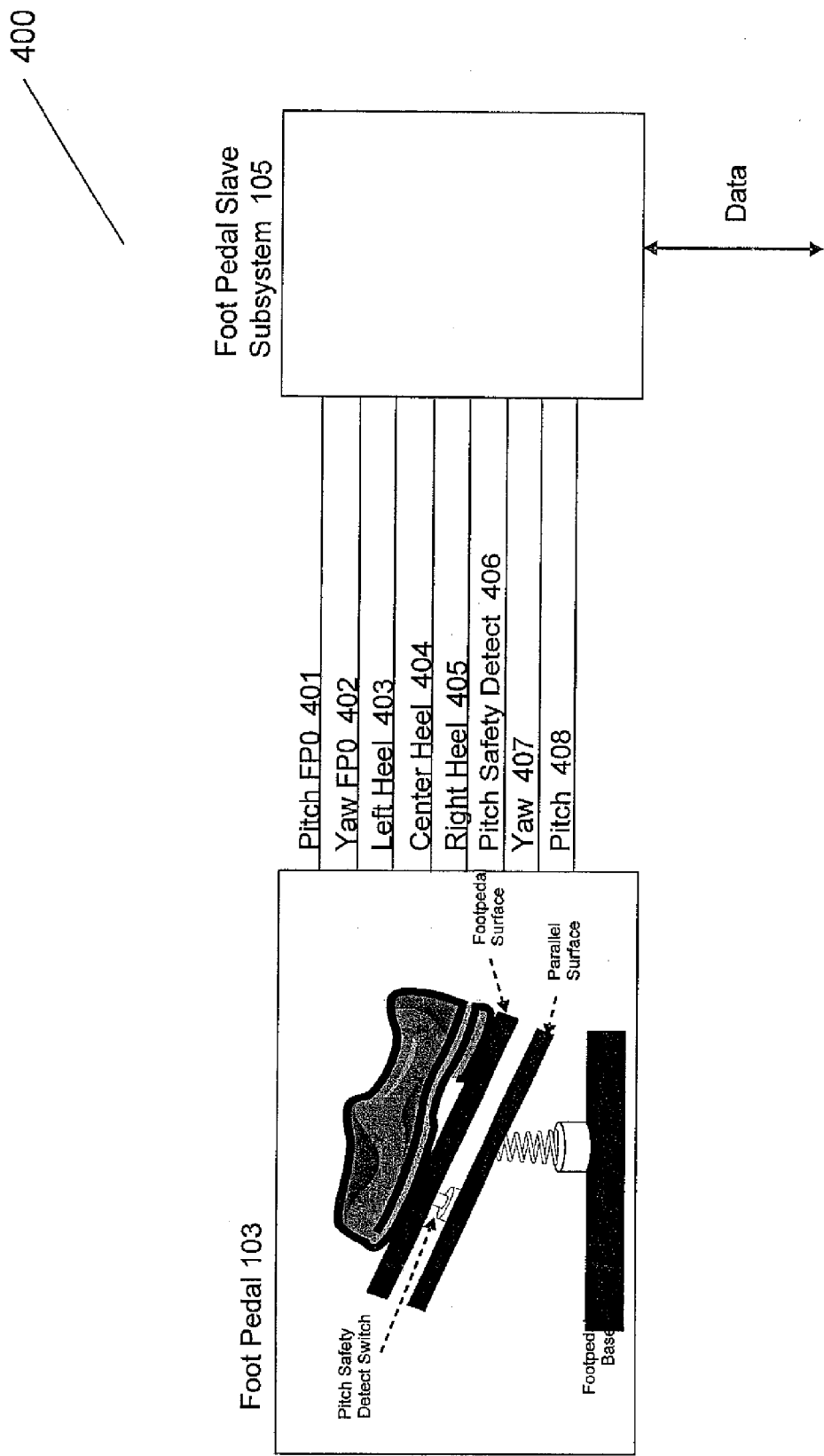
FIG. 4 shows a footpedal that may be employed in accordance with the current design.

FIG. 4 illustrates a footpedal 103 that may be employed in accordance with the current design. In the embodiment illustrated, the footpedal slave subsystem 105 receives one or more control signals from the footpedal 103. The control signals generated by the footpedal 103 may report the status of various physical and virtual switches contained within or other parameters such as yaw linear position and vertical linear position. The footpedal firmware within the footpedal slave subsystem 105 reads and processes the switch inputs.

The footpedal slave subsystem 105 produces a data stream representing control signals resulting from the button and switch positions triggered on the footpedal 103. The control signals are ultimately destined for the instrument host 120. Control signals may include but are not limited to position of a footpedal, such as left heel 403, center heel 404, right heel 405, pitch safety detect 406, pitch 407, and yaw 408 positions; button pushes or "stomp" values, or other appropriate states in the case of a footpedal. Moreover, predefined footpedal positions FP0, FP1, FP2, or FP3 (FPn) may be communicated. For example, pitch FP0 401 and yaw FP0 402 may be communicated when the footpedal slave subsystem becomes connected.

Control signals may be produced by other devices, such as test or monitoring equipment, and these control signals may be transmitted by the multiple channel design presented herein, either separate from or together with the control signals transmitted by the footpedal 103 and communications slave subsystem 107. Further control signals such as selector switch signals, transducer data, and/or sensor data may be transmitted by the communications slave subsystem 107 to the communications master subsystem 106. If transmitted separately, the wireless controller 102 and communications master subsystem 107 may receive the transmitted control signals via wireless communications network 130.

Figure 5:
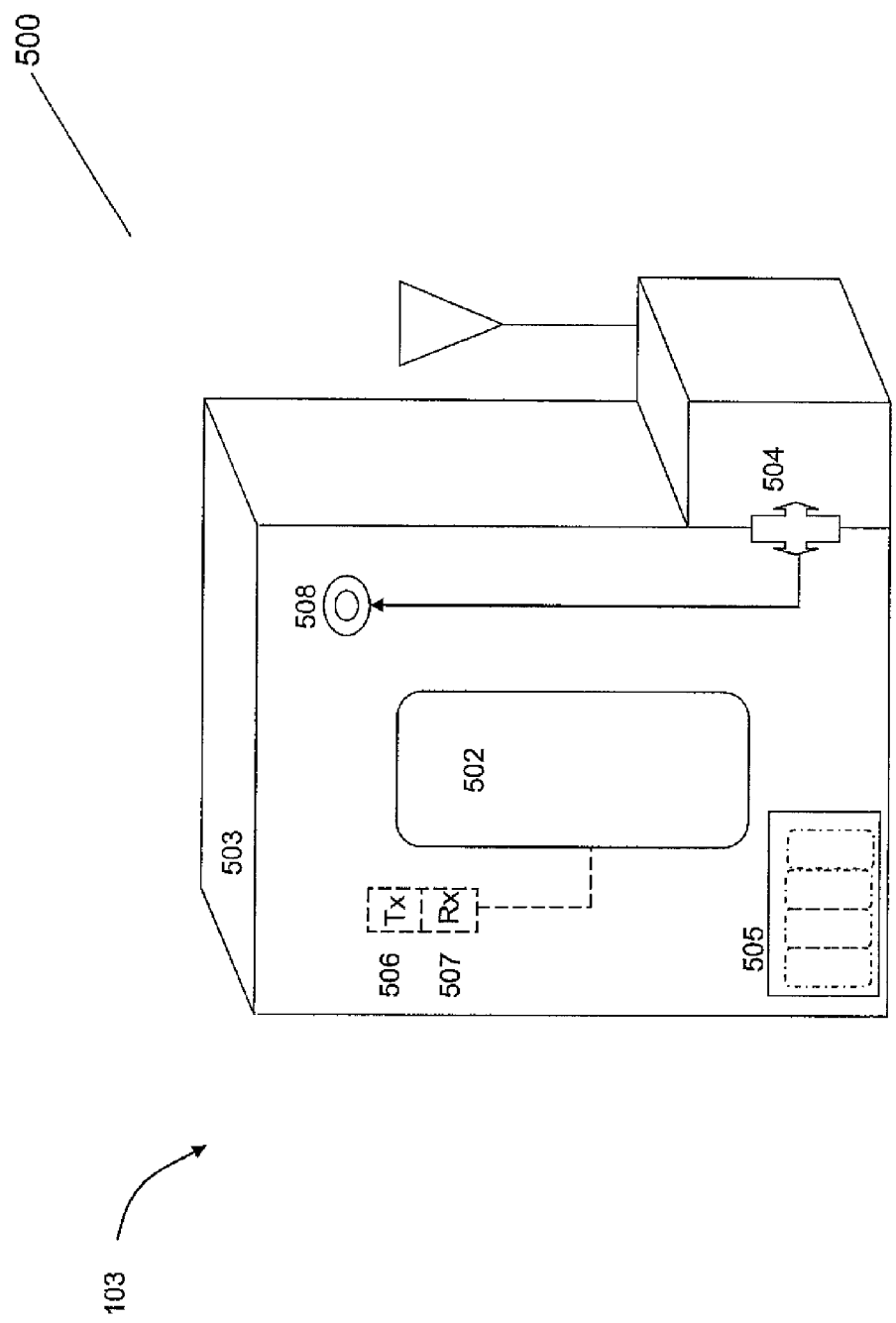
FIG. 5 shows the conceptual connections between the footpedal, base unit, and power source of the present design.

FIG. 5 shows the conceptual connections between the footpedal 103 and the base unit and power source. Footpedal 103 includes pedal 502, base 503, and communications interface 504 here shown at the side of the base 503. The footpedal 103 in this view includes batteries 505, typically rechargeable batteries. A transmitter 506 and receiver 507 are provided in the footpedal 103 in this embodiment and connect to the communications interface 504 to access the antenna, and in this embodiment a "connection LED" 508 is provided that is constantly on when the both wireless device 101 primary and backup data channels are available for operational use. When either channel becomes disconnected due to interference or other causes, the connection LED 508 may blink on and off, warning the user that one data channel is lost or disconnected and communication redundancy is not available. Blinking in this manner enables the surgeon to decide whether to continue the procedure or wait until the lost data channel is restored. Other notification methods may be employed, including but not limited to optical (e.g. one LED per channel) and audio notification methods.

The foregoing is not determinative or exclusive or inclusive of all components, interfaces, communications, and operational modes employable within the present design. The design presented herein and the specific aspects illustrated are meant not to be limiting, but may include alternate components while still incorporating the teachings and benefits of the invention, namely a wireless device communication management apparatus employing a wireless medical device, wireless controller, a communications network, and instrument host system to facilitate surgeons while performing procedures. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. A method for managing communications between a plurality of medical devices, comprising:

providing a wireless connection between at least two medical devices, the at least two medical devices comprising a primary medical device and a secondary medical device;

causing the primary medical device to transmit and the secondary medical device to receive state signals wirelessly across a plurality of communication data channels, wherein the plurality of communication data channels comprise a primary communication data channel and a backup communication data channel, wherein the state signals are transmitted and received on the primary communication data channel and duplicate state signals are transmitted and received on the backup communication data channel, and wherein the transmission of the state signals and the duplicate state signals alternates so that the primary communication data channel and the backup communication channel are not transmitting the signals at the same time;

monitoring the health and status of the plurality of communication data channels, wherein the health and status of the plurality of communication data channels comprises signal strength and quality for said data channels; and when signal strength or quality on both data channels drops below a threshold, switching from wireless transmission of the signals to transmission of the signals across a fixed cable.

2. The method of claim 1, wherein the primary medical device comprises an optical surgical device.

3. The method of claim 1, wherein the state signals and the duplicate state signals are transmitted with different protocols on the primary communication data channel and the backup communication data channel.

4. The method of claim 1, wherein the state signals comprise status of the primary medical device.

5. A connectivity management system, comprising:
a wireless controller configured to communicate over a plurality of communications data channels; and
a wireless medical device configured to communicate over the plurality of communications data channels; and
a fixed wired connection as an alternate communications path between the wireless controller and the wireless medical device,
wherein the wireless controller and wireless medical device are wirelessly connected to exchange state information across said plurality of communications data channels; the plurality of communication data channels comprise a primary communications data channel and a backup communications data channel;
the wireless controller and wireless medical device are arranged to transmit and receive the state signals on the primary communications data channel, transmit and receive duplicate state signals on the backup communications data channel, and transmit the state signals and the duplicate state signals alternately so that the primary communications data channel and the backup communications data channel are not transmitting the signals at the same time;
and the system is arranged to monitor the health and status of the plurality of communication data channels comprising signal strength or quality on both communications data channels, and to switch from wireless transmission of the signals to transmission of the signals across the fixed cable when the signal strength or quality on both data channels drops below a threshold.

6. The system of claim 5, wherein the wireless controller further comprises a connection to a host system, the connection configured to forward wireless medical device state information to the host system.

7. The system of claim 5, wherein said wireless medical device and the wireless controller are arranged to employ a wireless communications protocol enabling a plurality of observed device state parameters to be transmitted between the wireless medical device and the wireless controller.

8. The system of claim 5, wherein the wireless controller and the wireless medical device are arranged to transmit the state signals and the duplicate state signals with different protocols on the primary communications data channel and the backup communications data channel.

9. The system of claim 5, wherein the wireless controller further comprises a connection to a host system, the connection configured to forward wireless medical device state information to the host system.

10. The system of claim 5, wherein said wireless medical device is arranged to generate state information indicating a non-active state serving as a fail safe trigger.

11. A method for providing wireless communications for a wireless medical device, comprising:
    transmitting observed state information across a communications network comprising at least one primary and one secondary communication data channel, such that the state information is transmitted on the primary communication data channel and duplicate state information is transmitted on the secondary communication data channel, and such that the transmission of the state information and the duplicate state information alternates so that the primary communication data channel and the secondary communication data channel are not transmitting the information at the same time;
    monitoring the health and status of the plurality of communication data channels comprising signal strength or quality of both communication data channels; and
    switching from wireless transmission of the state information to transmission of the state information across a fixed cable when the signal strength or quality on both communication data channels drops below a threshold.

12. The method of claim 11, wherein transmitting further comprises providing state information comprising status of the wireless medical device for the purposes of controlling a host system.

13. The method of claim 11, wherein the wireless communications are between the wireless medical device and a wireless controller, and wherein the method further comprises generating and reporting an independent redundant fail safe trigger from the wireless medical device to the wireless controller.

14. The method of claim 11, wherein the state information and the duplicate state information are transmitted with different protocols on the primary communication data channel and the secondary communication data channel.

* * * * *